United States Patent [19]

Pukel et al.

[11] Patent Number: 4,507,391

[45] Date of Patent: Mar. 26, 1985

[54] METHOD FOR DETECTING THE PRESENCE OF $G_{D3}$ GANGLIOSIDE

[75] Inventors: Clifford S. Pukel, Flushing; Kenneth O. Lloyd, Bronx, both of N.Y.; Luiz R. Travassos, Sao Palo, Brazil; Wolfgang G. Dippold, Mainz, Fed. Rep. of Germany; Herbert F. Oettgen, New Canaan, Conn.; Lloyd J. Old, New York, N.Y.

[73] Assignee: Sloan-Kettering Institute for Cancer Research, New York, N.Y.

[21] Appl. No.: 365,065

[22] Filed: Apr. 2, 1982

[51] Int. Cl.$^3$ ............... G01N 33/54; C12N 15/00
[52] U.S. Cl. .................... 436/504; 436/520; 436/536; 436/542; 436/548; 436/804; 436/811; 436/813; 436/815; 436/828; 435/4; 435/7; 435/68; 935/110
[58] Field of Search ............... 436/548, 536–541, 436/501–504, 63, 64, 811, 813, 815, 518, , 520, 542; 435/4, 7, 68, 172; 935/110

[56] References Cited

U.S. PATENT DOCUMENTS 4,331,647 5/1982 Goldenberg .............. 424/1
4,361,544 11/1982 Goldenberg .............. 424/1

OTHER PUBLICATIONS

Dippold, W. G. et al, PNAS, USA, vol. 77, (10), pp. 6114–6118 (10–1980) Applicants' Publication.
Pukel C. S. et al, J. Exp. Med., vol. 155, pp. 1133–1147 (4-1982).
Yeh, M. Y. et al, Int. J. Cancer, vol. 29, pp. 269–275 (1982).
Reisfeld, R. A. Nature, vol. 298, pp. 325–326, (7-1982).
Steplewski, Z. et al, Cancer Research, vol. 41, pp. 2723–2727 (1981).
Woodbury, R. G. et al, Proc. Natl. Acad. Sci. USA, vol. 77 (4), pp. 2183–2187 (4-1980).
Mitchell, K. F. et al, Proc. Natl. Acad. Sci. USA, vol. 77 (12), pp. 7287–7291 (12-1980).
Morgan, A. C. et al, Hypridoma, vol. No. 1, pp. 27–36 (1981).
Yeh, M. Y. et al, Proc. Natl. Acad. Sci., USA, vol. 76, pp. 2927–2931 (1979).
Bumol, T. F. et al, Proc. Natl. Acad. Sci., USA, vol. 79, pp. 1245–1249 (2-1982).
Nudelman, E. et al, J. Biol. Chem. vol. 257, pp. 12,752–12,756 (11-1982). (Supplemental to Yeh).
Koprowski, H. et al, Proc. Natl. Acad, Sci., USA, vol. 75 (7), pp. 3405–3409 (1978).
Brown, J. P. et al, J. Biol. Chem., vol. 255 (11), pp. 4980–4983 (1980).
Brown, J. P. et al, Proc. Natl. Acad. Sci. USA, vol. 78 (1), pp. 539–543 (1-1981).
Wilson, B. S. et al, Int. J. Cancer, vol. 28, pp. 293–300 (1981).

Primary Examiner—Ben R. Padgett
Assistant Examiner—M. Moskowitz
Attorney, Agent, or Firm—Felfe & Lynch

[57] ABSTRACT

Mouse monoclonal antibody $AbR_{24}$ (Dippold et al., Proc. Natl. Acad. Sci. 77:6114–6118, 1980) has a high degree of specificity for human melanoma cells when tested on viable cultured cells using the PA-MHA serological assay. The antigen detected by this antibody has been isolated from melanoma cells and shown to be $G_{D3}$ ganglioside by compositional and partial structural analysis and by comparison with authentic $G_{D3}$ by thin layer chromatography (TLC). $AbR_{24}$ reacts with authentic $G_{D3}$, but not with any other ganglioside tested. Using TLC and reactivity with $AbR_{24}$, a wide range of cells and tissues was examined for the presence of $G_{D3}$. A new serological assay, termed glycolipid-mediated immune adherence (GMIA), was devised for assaying the reactivity of $AbR_{24}$ with gangliosides. Melanomas (cultured cells or tumor tissue) were shown to have $T_{D3}$ and $G_{M3}$ as major gangliosides. Other cells and tissues examined also contained $G_{D3}$, but usually only in low amounts. Melanomas (and MOLT-4, a T-cell line) were characterized by a simplified ganglioside profile with $G_{D3}$ and $G_{M3}$ as major components. The apparent discrepancy between the ubiquitous presence of $G_{D3}$ and the serological specificity of $AbR_{24}$ for melanoma cells can be explained in terms of localization and concentration of $G_{D3}$ in different cells.

12 Claims, 9 Drawing Figures

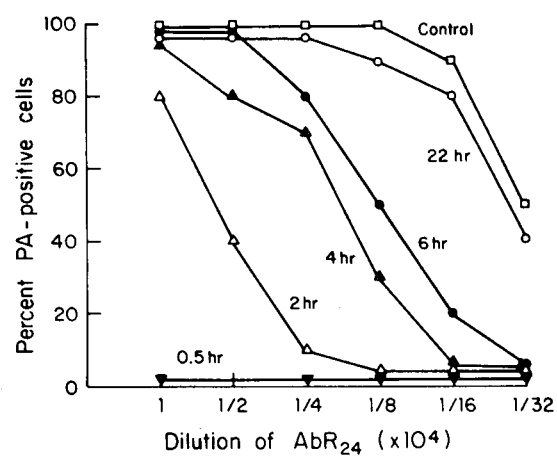
FIG. 1
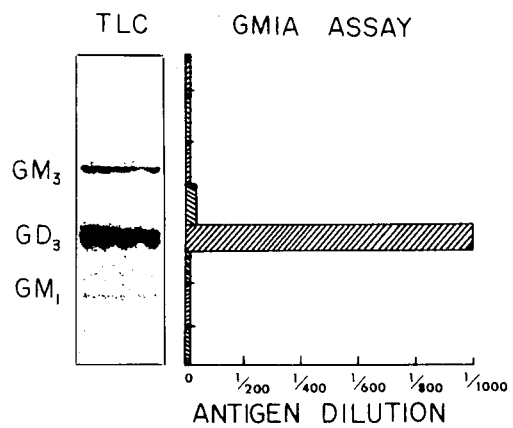
FIG. 2
FIG. 3
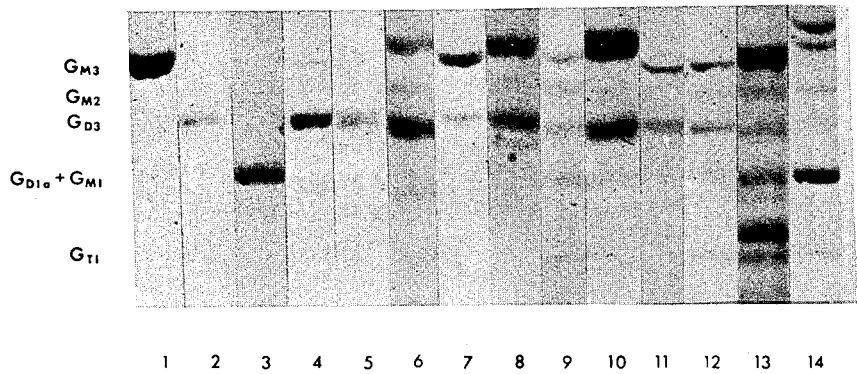

METHOD FOR DETECTING THE PRESENCE OF $G_{D3}$ GANGLIOSIDE

This work was partially supported by government funds under grants CA-08748, CA-21445 and CA-19765 from the U.S. Public Health Service. Therefore, the government has certain rights in this invention.

BACKGROUND

We have previously described a mouse IgG3 monoclonal antibody ($AbR_{24}$) with a high degree of serological specificity for cultured human melanoma cells (1). All melanoma cell lines examined and two astrocytomas were positive for the heatstable cell surface antigen detected by this antibody. Although choroidal melanocytes and brain had low levels of the antigen, a wide variety of other cells and tissues were unreactive. Three other monoclonal antibodies (Abs $C_5$, $I_{24}$, and $K_9$), having a similar restricted specificity, were derived from the same fusion. These antibodies showed the same strong reactivity with melanomas and lack of reactivity with epithelial cells, but had a slightly wider specificity range in that they also reacted weakly with MOLT-4 (a T-cell line), leukocytes and some fetal tissues.

The antigen detected by Ab $R_{24}$ is identified herein as $G_{D3}$— a previously characterized disialogangliodide. In comparison with other cells and tissues, melanomas have high levels of $G_{D3}$. Thus, these antibodies are useful in determining whether a tissue sample is a melanoma or not. This is particularly important for characterizing lesions. These antibodies can also be used in determining concentrations of $G_{D3}$ in serum, plasma, urine or other body fluids. This may aid in the early diagnosis of melanoma and possibly of other disorders where there are elevated glycolipid levels.

FIG. 1 time course for the reexpression of $AbR_{24}$-reactive antigen on SK-MEL-28 cells after neuraminidase treatment. Assay: PA-MHA.

FIG. 2 localization of $AbR_{24}$-reactive glycolipid on thin layer chromatography using glycolipid-mediated immune adherence (GMIA) assay. Acidic glycolipids from SK-MEL-28 cells were separated by TLC in solvent 1. Silica gel bands (1 cm wide) were scraped from the plate, extracted with C:M (1.2) and assayed for antigens by GMIA as described in the text.

FIG. 3 thin layer chromatography of acidic glycolipid fractions from a number of cell lines and tissues. Lane 1: $G_{M3}$; 2: $G_{D3}$; 3: $G_{M1}$; 4: SK-MEL-28 melanoma cell line; 5: $AbR_{24}$-reactive antigen isolated from SK-MEL-28; 6: SK-MEL-37 melanoma cell line; 7: SK-MEL-64 melanoma cell line; 8: MeWo; 9: SK-MEL-13 melanoma cell line; 10: melanoma (surgical specimen); 11: MOLT-4 T-cell line; 12: mouse eye; 13: SK-RC-7 renal cancer cell line; 14: adult human brain. Gangliosides were separated in solvent 1 and visualized with resorcinol-HCl.

FIG. 4 densiometric tracings of thin layer chromatograms of gangliosides from melanomas and other cells. A: SK-MEL-28 melanoma cell line; B: SK-MEL-37 melanoma cell line; C: SK-MEL-13 melanoma cell line; D: melanoma (surgical specimen); E: adult human brain; F: Raji B-cell line; G: MOLT-4 cell line; H: SK-RC-7 renal cell line. The amount of $G_{D3}$, as % of total ganglioside fraction, was calculated from the areas of the peaks and is indicated in each panel.

FIG. 5 inhibition of reactivity of $AbR_{24}$ with SK-MEL-28 melanoma cells by acidic glycolipid fractions from a variety of cell lines and tissues. Assay: PA-MHA.✛: $AbR_{24}$ control;✢: adult human spleen; ✦: adult human liver; 0: teleost eye; ■: SK-RC-7 renal cancer cell line; ▲: adult human brain; ◇: MeWo melanoma cell line; ◆: SK-MEL-29 melanoma cell line; ▼: SK-MEL-37 melanoma cell line; ▼: mouse eye; : MOLT-4 T-cell line; Δ: melanoma (surgical specimen); ●: SK-MEL-28 melanoma cell line.

FIG. 6 glycolipid-mediated immune adherence (GMIA) assay using $AbR_{24}$. Well A: $AbR_{24}$-reactive glycolipid isolated from SK-MEL-28 melanoma cell line; well B: $G_{D3}$ ganglioside; well C: no ganglioside; well D: $G_{M2}$ and $G_{M3}$ ganglioside mixture. Antibody: $AbR_{24}$ (1:1000).

FIG. 7 detection of $G_{D3}$ ganglioside by $AbR_{24}$ in GMIA assays. $AbR_{24}$ dilutions are indicated in the figure.

FIG. 8 detection of $G_{D3}$ ganglioside on TLC plates by reactivity with $AbR_{24}$ and $^{125}I$-Protein A. Right side: gangliosides visualized with resorcinol-HCl reagent; left side: gangliosides reacting with $AbR_{24}$ and 125I-Protein A. Lane 1: $AbR_{24}$-reactive ganglioside; Lane 2: gangliosides extracted from adult human brain. Solvent 2.

FIG. 9 proposed pathways for the biosynthesis of gangliosides [modified after Yu and Ando (32)].

DETAILED DESCRIPTION

Tissue Culture

Figure 4:
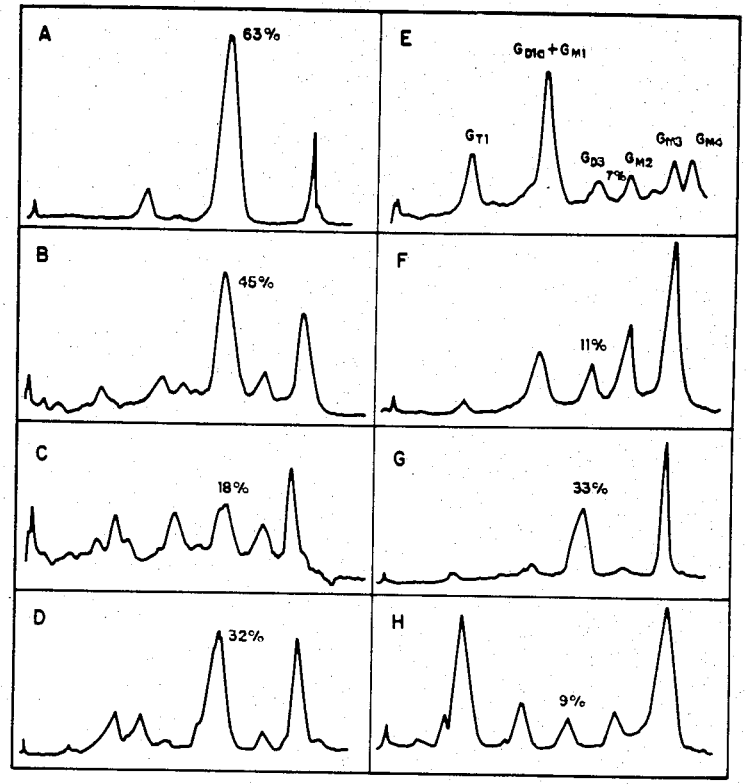

For derivations and culture of melanoma and other cells see references 1-4. Normal and malignant tissue was obtained from surgical or postmortem specimens.

Monoclonal Antibodies

Mouse monoclonal antibodies $AbR_{24}$, $AbC_5$, $AbI_{12}$, and $AbN_9$ have been previously described (1), $AbR_{24}$ and $AbC_5$ are IgG3 antibodies and $AbI_{12}$ and $AbN_9$ are IgG2b and IgG1 antibodies, respectively.

Glycolipids $G_{D3}$ was obtained from Dr. Y-T. Li, Tulane University, New Orleans (5). $G_{M3}$ and $G_{M2}$ were obtained from Drs. S. Kundu and D. M. Marcus, Baylor University, Houston, TX. $G_{M1}$, $G_{D1a}$, $G_{T1}$ were purchased from Supelco, Inc., Bellefonte, PA. Lactosylceramide was purchased from Glycolipid Biochemical Co., Birmingham, Al.

Serological assays for melanoma cell surface antigens

Reactivity of $AbR_{24}$ and $AbC_5$ with cell surface antigens of melanoma cells was determined with cultured cells growing in the wells of Microtest plates (Falcon 3034) using a red cell rosetting method (3) in which indicator cells are human O red cells (RBC) to which *Staphylococcus aureus* protein A is conjugated (PA-MHA). $AbI_{12}$ and $AbN_9$ were assayed using a modification of this method in which rabbit anti-mouse Ig-conjugated indicator cells were used (IgG-MHA).

Enzyme treatment

Melanoma cells growing as monolayers in microtest plates as described above were washed with Hank's balanced salt solution (HBSS, Microbiological Associates) and then treated with *Vibro cholerae* neuraminidase (Calbiochem) or β-galactosidase (Sigma, Type VII)

using 1 U/well in 10 μl of HBSS. After incubation for 1 hr at 37°, the cells were washed four times with PBS - 2% gamma globulin (GG)-free FBS and assayed for reactivity with antibody using the PA- or IgG-MHA assays.

Isolation of glycolipids

Glycolipids were isolated initially by a modification of the method of Saito and Hakomori (6), and separated into neutral and acidic fractions by DEAE-Sephadex chromatography (7). Acidic glycolipids (gangliosides) were subsequently isolated directly from chloroform-methanol (C-M) extracts by DEAE-Sephadex chromatography and alkaline hydrolysis (7). Briefly, cells were homogenized in C-M (2:1) and after filtration were re-extracted with C-M (1:1). After evaporating and redissolving the extract in C-M (1:2), it is filtered, evaporated and dialyzed against distilled ice water for 24 hours in the cold. After dialysis, samples were evaporated, dissolved in C-M-H$_2$O (30:60:8) and applied to a DEAE-Sephadex column (equilibrated with C-M-0.8 M Na acetate); (30:60:8). After washing the column with C-M-H$_2$O (30:60:8), acidic lipids were eluted with C-M-0.8 M Na acetate (30:60:8), evaporated and dialyzed as before. The acidic fraction was then hydrolyzed with 0.1 N NaOH in methanol for 3 hours at 37° C., dialyzed against cold water (48 hours), evaporated, and dissolved in C-M (4:1). The solution was applied to a Biosil A column which had previously been washed with C-M (4:1). After eluting impurities with C-M (4:1), gangliosides were eluted with C-M (1:2).

Thin layer chromatography (TLC)

Silica gel plates (Rediplates, Fisher Scientific Co.) were activated by heating at 120° C. for 1 hour. Solvents used for developing chromatograms were n-propanol-NH$_4$OH-H$_2$O, 60:9.5:11.5 (solvent 1) as in ref. 8 and chloroform: methanol:2.5 N NH$_4$OH, 60:40:9 (solvent 2). Once the solvent had migrated 12 cm from the origin, the plate was removed and air-dried for 12-15 minutes at 110°-120° C., cooled to room temperature and sprayed with resorcinol-HCl (9). For preparative analysis, plates were dried at room temperature in an air flow hood for 2-3 hours. Bands were visualized with iodine vapor, outlined and silica gel scraped from the plate. The gel was then extracted twice with 40 ml of C-M-H$_2$O (50:50:15), with a small amount of Dowex 50 (Na$^+$). The suspension was centrifuged at 1000 rpm for 15 minutes and the solution filtered, evaporated, redissolved in C-M (4:1) and applied to a Biosil A column as described above. Impurities were eluted with C-M (4:1) and adsorbed gangliosides were then eluted with C-M (1:2).

Carbohydrate analysis

Lipid-bound sialic acid in cell pellets was determined on C:M (2:1 and 1:2) extracts after hydrolysis in 0.1 N HCl at 80° for 1 hour as described by Warren (10). Sugars were analyzed after methanolysis (methanolic 1.0 N HCl at 100° for 16 hours) as their O-trifluoroacetates (11); N-acetylneuraminic acid was identified by the same procedure after methanolysis in 1.0 N HCl at 80° for 1.0 hour.

Serological assays for glycolipids (i) Passive hemmaglutination assay (cf. 12)

Glycolipids (6 μg sialic acid) were dissolved, aliquoted into tubes (10×75 mm) and dried in a dessicator with P$_2$O$_5$ in vacuo. To each tube, 200 μl of PBS was added, the sides of the tube scraped and the solutions sonicated for 15 min at 50° C. After transfer to a larger tube, 0.8 ml of PBS was added. The glycolipid solution was added slowly in a dropwise fashion to a 2% suspension of human O-RBC in PBS. After 1 hour at 37° C., with one mixing after 30 minutes, the cells were washed twice with PBS (12 ml each wash). Reactivity was tested by mixing a suspension of the treated RBC and appropriately diluted AbR$_{24}$ (50 μl each) in microtiter plates. After 1-2 hours at 4° C., the agglutination reactions were scored visually.

(ii) Antibody inhibition assay

Glycolipids (6 μg sialic acid), dissolved in C-M (1:2), were aliquoted into tubes (6×50 mm) and dried as in the previous assay. AbR$_{24}$ (1:2×10$^4$) was added 30 μl) and the tubes were vortexed, incubated for 30 minutes at room temperature, and then for 30 minutes at 4° C. Tubes were centrifuged for 20 minutes at 2000 rpm and the supernatants removed and serially diluted. These samples were immediately transferred to formaldehyde-fixed SK-MEL-28 target cells. [The formaldehyde fixation was carried out by treating cells growing in the wells of microtest plates (Falcon 3034) with 0.33% HCHO in PBS. This treatment does not alter reactivity with AbR$_{24}$ and provides a store of readily available source of target cells]. Antibody reactivity was detected with the PA-MHA assay. Unabsorbed antibody served as a positive control.

(iii) Glycolipid-mediated immune adherence assay (GMIA)

A solution of glycolipids in 95% ethanol was added to the wells of microtest plates (Falcon 3034; 10 μl per well) and the plates were dried in a dessicator in vacuo with P$_2$O$_5$ for 45 minutes. Approximately 100 ng of lipid-bound sialic acid was found to be the optimal amount for efficient adsorption and maximal reactivity with antibody. Wells were then washed three times with PBS- 2% GG-free FBS (10 ml/wash), and the plates blotted with gauze. Diluted antibody (in PBS with 5% GG-free FBS) was added to the wells and incubated for 45 minutes at room temperature. Plates were blotted, washed four times with PBS- 2% GG-free FBS, and blotted again. Ten μl of a 0.2% suspension of Protein A-conjugated O-RBC were added to the wells. The plates were incubated for 30 minutes at room temperature. After blotting, the plates were washed twice with PBS- 2% GG-free FBS, blotted once again and read under the light microscope. Reactions were scored according to the proportion of the well which was covered by red cells. A test was read as negative when wells showed no adhering cells or only a thin ring of cells around the perimeter.

(iv) Detection of serologically-reactive glycolipid after separation by thin layer chromatography.

Serological reactivity of glycolipids separated by thin layer chromatography was tested using a modification of the method of Magnani et al. (13) in which $^{125}$I-Protein A was used to detect the bound antibody. After chromatography in solvents 1 or 2 thin layer sheets were washed in PBS buffer containing 1% polyvinyl-pyrolidone and treated with AbR$_{24}$ (1:1500) for 6 hours at 4° C. After washing in PBS, the plate was treated with $^{125}$I-Protein A (10 μCi/μg; 7×10$^5$ cpm/ml), prepared according to the procedure of Hunter and Greenwood (14). After standing for 12 hours at 4° C., the plate was washed in PBS, air-dried and exposed to X-Omat R film with a Cronex intensifier screen for 2-6 hours.

RESULTS

Alteration of AbR$_{24}$ serological reactivity and kinetics of antigen restitution after neuraminidase treatment of SK-MEL-28

After treatment with neuraminidase (*Vibrio cholerae*), SK-MEL-28 melanoma cells no longer reacted with AbR$_{24}$ in PA-MHA assays (Table I). Reactivity with AbC$_5$ [an antibody with a serological specificity similar to that of AbR$_{24}$ (1)] was also lost. Reactivity with AbN$_9$ and AbI$_{12}$ which recognize serologically unrelated determinants on glycoproteins of SK-MEL-28 (deposited as ATCC No. HTB72) was unaffected by neuraminidase. Enzyme-treated cells did not show non-specific reactivity with either Protein A- or with anti-mouse Ig-indicator cells. β-Galactosidase had no detectable effect on the reactivity of SK-MEL-28 cells with AbR$_{24}$ or AbC$_5$ (Table I). These results show that sialic acid constitutes an important part of the antigenic determinant recognized by antibodies AbR$_{24}$ and AbC$_5$.

Serological reactivity of AbR$_{24}$ with SK-MEL-28 remained undetectable for 30 minutes after neuraminidase was removed and replaced with MEM-FBS. Continued incubation in this medium at 37° resulted in a partial return of AbR$_{24}$ reactivity after 2 hours and complete recovery of serological reactivity after 22 hours (FIG. 1).

Isolation of AbR$_{24}$-reactive antigen from SK-MEL-28 melanoma cells and its identification as G$_{D3}$ ganglioside Glycolipids were isolated from cultured melanoma cells (SK-MEL-28) by chloroform-methanol (C-M) extraction and Florisil chromatography of their acetates as described by Saito and Hakomori (5) and the glycolipid preparation was fractionated into neutral and acidic components by DEAE-Sephadex chromatography. Inhibitory activity against AbR$_{24}$ antibody (assayed with PA-MHA) was found to reside entirely in the acidic glycolipid fractions.

In subsequent experiments, acidic glycolipids from SK-MEL-28 cells were isolated directly by fractionating the C-M extract on DEAE-Sephadex (6) and eliminating contaminating phospholipids by alkaline hydrolysis. Individual gangliosides in this mixture were isolated by preparative thin layer chromatography in solvent 1 (8). By scraping a series of silica gel bands from the plates and extracting the glycolipids, the antigenic activity was located in the major acidic glycolipid band which migrated just above G$_{M1}$ and G$_{D1a}$ (FIG. 2). In the data presented in FIG. 2, the antigenic activity of fractions was measured by the GMIA assay. Similar results were obtained by antibody inhibition tests using the PA-MHA assay with AbR$_{24}$ and SK-MEL-28 target cells.

The isolated AbR$_{24}$-reactive glycolipid was identified as G$_{D3}$ [NANA(2→8)NANA (2→3)Galβ(1→4)Glc-ceramide] by the following criteria: (i) carbohydrate analysis of the purified glycolipid showed that it contained glucose, galactose and N-acetylneuraminic acid in a ratio of 1.0:1.09:2.11 with only a trace (<0.1) of hexosamine, (ii) partial hydrolysis of the ganglioside with *Vibrio cholerae* neuraminidase (3 hours at 37° C.) resulted in the formation of two components comigrating on thin layer chromatograms with G$_{M3}$ and lactosylceramide, (iii) the purified melanoma glycolipid comigrated with authentic G$_{D3}$ in thin layer chromatography (FIG. 3) and (iv) AbR$_{24}$ reacted with authentic G$_{D3}$, but not with any of the other standard gangliosides tested (see below).

Distribution of G$_{D3}$ in melanoma and non-melanoma cell lines, and in normal and malignant tissues (i) Thin layer chromatographic patterns of gangliosides from various sources Total ganglioside fractions were prepared from a large variety of tumor cell lines, fresh tumors and normal tissues. When these extracts were fractionated by TLC and the gangliosides detected using the resorcinol reagent, it became evident that melanomas have a characteristic pattern of gangliosides. In all the melanoma cell lines examined, glycolipids comigrating with G$_{D3}$ and G$_{M3}$ were prominent acidic glycolipids, with G$_{D3}$ being the major component in many of these cell lines (FIG. 3 and FIG. 4). G$_{D3}$ was also a prominent ganglioside in extracts of mouse eye and bovine choroid. With the exception of MOLT-4 (a T-cell line), none of the other cells or tissues had G$_{D3}$ as the major component. Extracts of fresh melanoma tumors gave ganglioside patterns resembling SK-MEL-28, with G$_{D3}$ and G$_{M3}$ predominating (FIG. 3). Most melanoma cell lines gave this simplified pattern, but some showed a more complex profile in which higher gangliosides were detected in appreciable amounts (FIGS. 3 and 4). G$_{D3}$ constituted 18–63% of the total ganglioside fraction in the melanoma cell lines examined (FIG. 4). Most melanoma cells lines and specimens had values in the 30–50% range. These values compared with 7% in adult human brain, 9% in a renal cancer cell line (SK-RC-7), 11% in RAJI cells (a Burkitt's lymphoma) and 33% in MOLT-4 cells (FIG. 4). In terms of the serological reactivity of AbR$_{24}$, it is important to note that melanomas, in addition to having higher proportions of G$_{D3}$ in their glycolipid fraction, also have higher total ganglioside levels. This is evident from a determination of the levels of lipid-bound sialic acid in a number of cell lines. In melanomas the values ranged from 0.039–0.063μ mole/0.1 ml cells (determined on 9 lines). RAJI, MOLT-4 and renal cancer cells (3 lines) had lipid-bound sialic acid values of 0.011±0.003, 0.013±0.006 and 0.025–0.029μ mole/0.1 ml cells, respectively.

(ii) Detection of G$_{D3}$ in cell lines and tissues using AbR$_{24}$ antibody

G$_{D3}$ levels in a large variety of cells and tissues were estimated using R$_{24}$ antibody. Four assay methods were used: (a) passive hemagglutination, (b) antibody inhibition, (c) a new method, GMIA, devised to combine the simplicity of the MHA method with the ability of glycolipids to adsorb to plastic and (d) a method using $^{125}$I-Protein A to detect AbR$_{24}$ reacting with G$_{D3}$ on TLC chromatograms. The sensitivity of the assays varies considerably; the passive hemagglutination assay is the least sensitive and the $^{125}$I-PA method the most sensitive (Table II).

Figure 5:
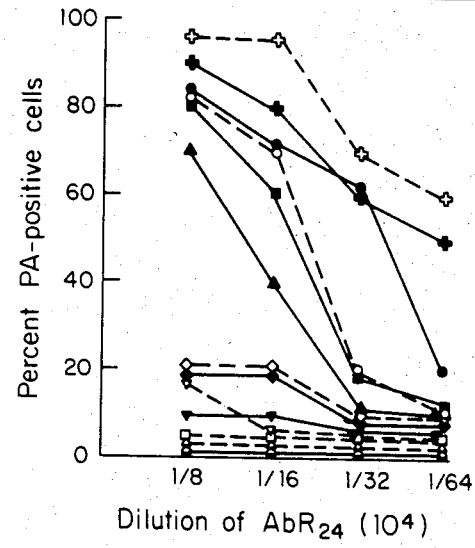
Figure 6:
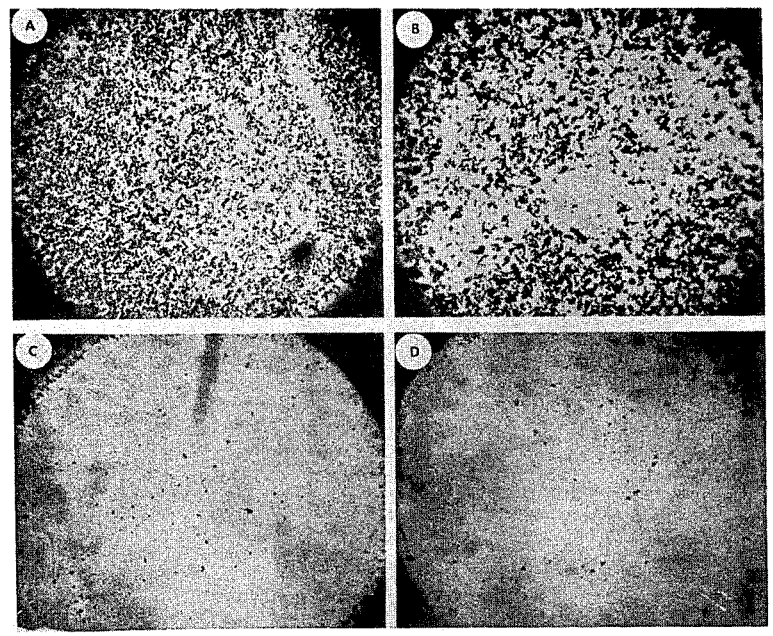
Figure 8:
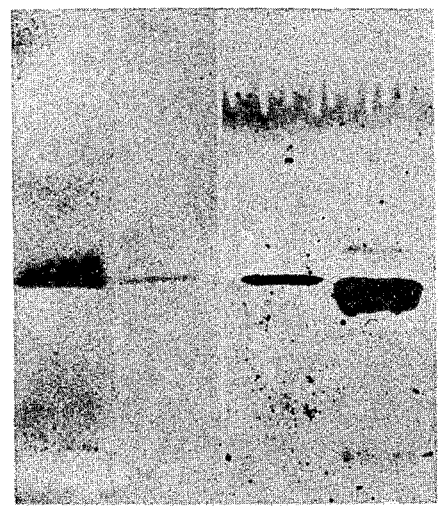
Figure 7:
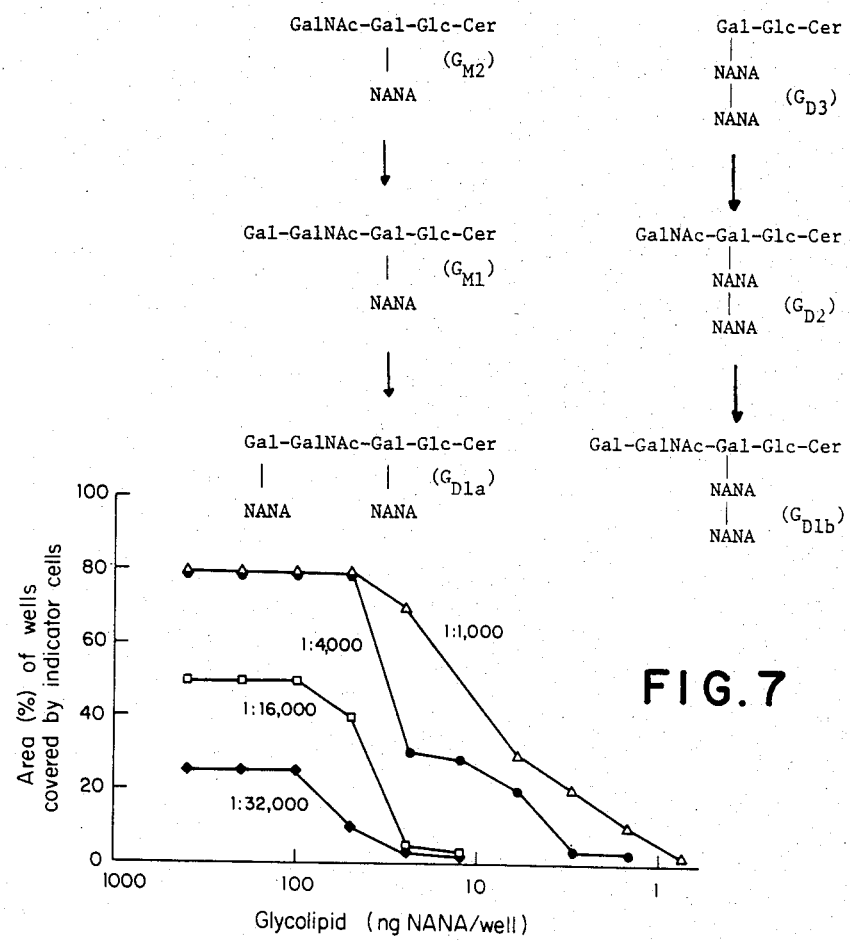

Using the least sensitive detection method (passive hemagglutination), G$_{D3}$ could be detected in extracts of melanoma cell lines and melanoma tissue, but not in other sources (Table II). More sensitive assays (inhibition of PA-MHA and GMIA methods) showed that G$_{D3}$ was detectable in a wider range of cells (bovine choroid, mouse eye, fetal and adult human lung, RAJI B-cell line, MOLT-4 T-cell line, RT-4 bladder cancer cell line and AJ astrocytoma cell line). A typical inhibition experiment is presented in FIG. 5 and the data are summarized in Table II. Using the GMIA method it was found that walls coated with R$_{24}$-reactive glycolipids from melanoma (FIG. 6A) or authentic $G_{D3}$ gave strongly positive reactions (FIG. 6B); some quantitative data on this reaction are shown in FIG. 7. Other purified glycolipds ($G_{M1}$, $G_{D1a}$, $G_{M3}$ and $G_{M2}$) were unreactive in this assay (Table II and FIG. 6D). $AbR_{24}$ added alone was also unreactive (FIG. 6C). Application of this method to acidic glycolipids extracted from other cells gave approximately the same results as inhibition assays (Table II). In contrast to the restricted distribution of $G_{D3}$ determined by these methods, the $^{125}$I-Protein A method detected $G_{D3}$ in all the cells and tissues examined (Table II). That the $AbR_{24}$-reactive component detected in these tissues and cells was in fact $G_{D3}$ was indicated by its co-migration with authentic $G_{D3}$ (in two solvent systems), and by the finding that another protein A-binding monoclonal antibody ($AbI_{12}$), detecting an unrelated glycoprotein specificity, was unreactive.

DISCUSSION

Mouse monoclonal antibody $R_{24}$, which shows a high degree of serological specificity for cell surface antigens of melanoma cells, recognizes a disialoganglioside—$G_{D3}$. Past studies have shown that antibodies to gangliosides have been difficult to raise (15). This may have to do with the fact that most gangliosides are constituents of the species being immunized and also, because in situ sialidase activity may destroy ganglioside immunogenicity (16). In this regard, it might be significant that the mouse from which $AbR_{24}$ was developed had been extensively immunized over a period of six months with melanoma cells (SK-MEL-28) having a very high $G_{D3}$ content. Two other monoclonal antibodies recognizing gangliosides have recently been described (17,18). One reacts specifically with chicken neuronal cells and is directed against one of the higher gangliosides present in the GQ fraction (17); the second is directed against human colon carcinoma and recognizes an as yet uncharacterized monosialoganglioside (18).

We have shown that $G_{D3}$ is a prominent ganglioside in cultured melanoma cells and in melanoma tissue. When compared with other cells, melanoma cells also possess relatively high total ganglioside levels. As shown by others, $G_{D3}$ is present in small amounts in most mammalian tissues, but it is a major ganglioside in the retina, where it comprises between 30-40% of the gangliosides (19). In adult human brain, $G_{D3}$ represents about 8-10% of the total ganglioside content (19). Levels of $G_{D3}$ may be higher in fetal brain, considering that in fetal rat brain (15-17 days gestation) $G_{D3}$ represents about 50% of the total ganglioside content, falling rapidly to about 10% by day 20 (20). Portoukalian and coworkers (21) have also reported that $G_{D3}$, identified by TLC and carbohydrate analysis, is a major constituent of melanomas. They showed that the proportion of $G_{D3}$ varied from 31.0% to 57.2% of the ganglioside fraction in the four different melanoma specimens examined. From these results, as well as our own analysis, one can conclude that $G_{D3}$ ganglioside is a prominent component of malignant melanoma. Whether normal melanocytes have high levels of $G_{D3}$ is at present unclear. Normal choroidal melanocytes show weak reactivity with $AbR_{24}$ in direct serological tests (titer 1:100) as compared to the strong reactivity of melanoma cells (titer of $1:5 \times 10^4$-$10^5$) (1). With the recent development of a method for culturing skin melanocytes (22), it will now be possible to make direct comparison of the $G_{D3}$ content of melanocytes and melanomas. Although a precise biological function for $G_{D3}$ remains to be determined, it has been suggested that $G_{D3}$ has a role in serotonin binding (23,24).

In examining the TLC patterns of the gangliosides isolated from different melanoma cell lines, we noticed considerable variation in the proportion of the various gangliosides. In most cell lines $G_{D3}$ and $G_{M3}$ were the predominant gangliosides (FIGS. 3 and 4). A few melanoma cell lines showed a more complex pattern with $G_{M2}$ and some higher gangliosides being better represented; whether these differences in ganglioside profiles correlate with biological characteristics (e.g. differentiation state) of the tumor needs to be determined. In general, melanomas exhibit a distinctive ganglioside profile. Of the other cells and tissues examined, only the T-cell line MOLT-4 showed a similar profile, and this may be another example of antigens shared by T-cells and cells of neuroectodermal origin e.g. Thy-1 (25). Gangliosides derived from bovine choroid and mouse eye had more complex patterns, with $G_{D3}$ being only one of three or four prominent components.

It is very evident from the analysis of extracted glycolipids that the presence of $G_{D3}$ ganglioside is by no means restricted to melanoma cells—it is ubiquitous. Yet using direct serological assays for cell surface antigens, only melanomas, choroidal melanocytes, and astrocytomas were reactive with $AbR_{24}$ (1). Even using sensitive absorption tests, only normal brain of other cells and tissues tested absorbed $AbR_{24}$. A number of explanations for the apparent discrepancy between the serological finding and the biochemical data presented here can be suggested. First, it is possible that $G_{D3}$ is not a cell surface constituent of most non-melanoma cells. It is well established that $G_{D3}$ is a biosynthetic precursor of other gangliosides (FIG. 9) and would therefore be located mainly within the cell, probably in the Golgi apparatus where the glycosyl transferases responsible for glycolipid synthesis are found (26,27). As our biochemical studies were carried out on whole cell or tissues the results are certainly compatible with this explanation. Another possibility is that $G_{D3}$ is present at the cell surface of $R_{24}$-negative cells but is not available for reaction with antibody. This phenomenon has been found with other cell membrane glycolipids e.g. globoside is a major glycolipid of erythrocyte membrane but erythrocytes react only weakly with anti-globoside antibody (28). It is also possible, of course, that $G_{D3}$ is not expressed on the surface of most non-melanoma cells in amounts that are detectable by the serological tests used. It is important to note that the cell types which reacted with $AbR_{24}$ in both direct and absorption tests have both a high lipid-bound sialic acid content and have $G_{D3}$ as a prominent glycoside.

Figure 9:
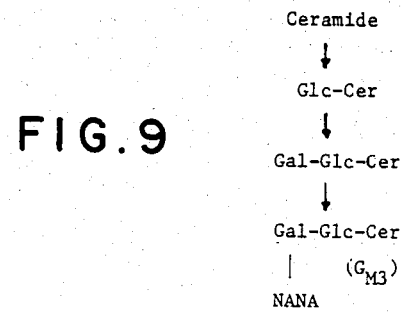

What might be the mechanism of the accumulation of $G_{D3}$ and $G_{M3}$ in melanoma cells? One possible explanation is that melanoma cells have low levels of N-acetylgalactosaminyl transferase(s) which would result in the accumulation of the normal substrates for the enzyme(s) i.e. $G_{M3}$ and $G_{D3}$ (FIG. 9). In bovine thyroid, a single N-acetylgalactosamine-transferase is though to act on both $G_{D3}$ and $G_{M3}$ to form $G_{D2}$ and $G_{M2}$, (27) and low levels of this enzyme in melanomas could explain the ganglioside pattern we observed. Among other possible explanations are that melanomas have high levels of β-N-acetylgalactosaminidase which would result in increased degradation of $G_{M2}$ and $G_{D2}$ or that melanomas have elevated levels of certain sialytransferases, resulting in increased synthesis of $G_{D3}$ and $G_{M3}$. It is significant in this regard that malanoma patients have increased serum sialyltransferase levels (29). Enzyme levels in tumor tissue have not yet been studied, although the fact that the glycoproteins of human melanoma cell lines have increased sialylation as compared to the glycoproteins of other cell types (30) suggests increased activity of this enzyme in melanoma.

ABBREVIATION USED IN THIS APPLICATION

TLC: thin layer chromatography; MHA: mixed hemagglutination assay; C-M: chloroform-methanol; FBS: fetal bovine serum; NANA: N-acetylneuraminic acid; Gal: D-galactose; Glc: D-glucose; GalNAc: N-acetyl-D-galactosamine; Cer: ceramide; $G_{M1}$: βGal 1–3 GalNAc 1→4 βGal[3←2 NANA] 1→4 Glc-Cer; $G_{M3}$: NANA 2→3 βGal 1→4 Glc-Cer; $G_{D3}$: NANA 2→8 NANA 2→3 βGal 1→4 Glc-Cer; $G_{D1a}$: NANA 2→3 βGal 1→3 GalNAc β1→4 Gal [2←2 NANA] Glc-Cer; $G_{M2}$: βGalNAc 1→4 βGal [3→2 NANA]Glc-Cer. $G_{T1a}$: NANA 2→8 NANA 2→3 βGal 1→3 GalNAc β1→4 Gal[3←2 NANA]Glc-Cer. [Nomenclature of Svennerholm (31)].

REFERENCES

1. Dippold, W. G., Lloyd, K. O., Li, L. T. C., Ikeda, H., Oettgen, H. F. and Old, L. J. (1980) Cell surface antigens of human malignant melanoma: Definition of six antigenic systems with monoclonal antibodies. *Proc. Natl. Acad. Sci. USA* 77:6114.
2. Carey, T. E., Takahashi, T., Resnick, L. A., Oettgen, H. F. and Old, L. J. (1976) Cell surface antigens of human malignant melanoma: mixed hemadsorption assays for humoral immunity to cultured autologous melanoma cells. *Proc. Natl. Acad. Sci. USA* 73:3278.
3. Pfreundschuh, M., Shiku, H., Takahashi, T., Ueda, R., Ransohoff, J., Oettgen, H. F. and Old, L. J. (1978) Serological analysis of cell surface antigens of malignant brain tumors. *Proc. Natl. Acad. Sci. USA* 75:5122.
4. Ueda, R., Shiku, H., Pfreundschuh, M., Takahashi, T., Li, L. T. C., Whitmore, W. F., Oettgen, H. F. and Old, L. J. (1979) Cell surface antigens of human renal cancers defined by autologous typing. *J. Expl. Med.* 150:564.
5. Itoh, T., Li, Y-T., Li, S-C. and Yu, R. K. (1981) Isolation and characterization of a novel monosialosylpentahexosyl ceramide from Tay-Sachs brain. *J. Biol. Chem.* 250:105.
6. Saito, T. and Hakomori, S. (1971) Quantitative isolation of total glycolipids from animal cells. *J. Lipid Res.* 12:257.
7. Yu, R. K. and Ledeen, R. W. (1972) Gangliosides of human bovine and rabbit plasma. *J. Lipid Res.* 13:680.
8. Watanabe, K., Powell, M. E. and Hakomori, S. (1979) Isolation and characterization of gangliosides with a new sialosyl linkage and core structure. II. Gangliosides of human erythrocyte membranes. *J. Biol. Chem.* 254:8223.
9. Svennerholm, L. (1957) Quantitative estimation of sialic acids. II. A colorimetric resorcinol-hydrochloric acid method. *Biochim. Biophys. Acta* 24:604.
10. Warren, L. (1963) Thiobarbituric acid assay of sialic acids. *Methods in Enzymol.* 6:463.
11. Zanetta, J. P., Breckenridge, W. C. and Vincendon, G. (1972) Analysis of monosaccharides of the O-methylglycosides as trifluoroacetate derivatives. *J. Chromatogr.* 69:291.
12. Yokoyama, M., Trams, E. G. and Brady, R. O. (1963) Immunochemical studies with gangliosides. *J. Immunol.* 90:372.
13. Magnani, J. L., Smith, D. F. and Ginsburg, V. (1980) Detection of gangliosides that bind cholera toxin: direct binding of $^{125}$I-labeled toxin to thin-layer chromatograms. *Anal. Biochem.* 109:366.
14. Hunter, W. M. and Greenwood, F. C. (1962) Preparation of iodine-131 labeled human growth hormone of high specific acitivity. *Nature* 194:495.
15. Rapport, M. M. and Graf, L. (1969) Immunochemical reactions of lipids. *Prog. Allergy* 13:273–331 (1969).
16. Kundu, S. K., Marcus, D. M. and Veh, R. W. (1980) Preparation and properties of antibodies to $G_{D3}$ and $G_{M1}$ gangliosides. *J. Neurochem.* 34:184.
17. Eisenbarth, G. S., Walsh, F. S. and Nirenberg, M. (1979) Monoclonal antibody to a plasma membrane antigen of neurons. *Proc. Natl. Acad. Sci. USA* 76:4913.
18. Magnani, J. L., Brockhaus, M., Smith, D. F., Ginsburg, V., Blaszcyzuk, M., Mitchell, K. F., Steplewski, Z. and Koprowski, H. (1981) A monosialoganglioside is a monoclonal antibody-defined antigen of colon carcinoma. *Science* 212:55.
19. Urban, P. F., Harth, S., Freysz, L. and Dreyfus, H. Brain and retinal ganglioside composition from different species by TLC and HPTLC. in Structure and Function of Gangliosides. *Adv. Exp. Med. Biol.*, ed. L. Svennerholm (Plenum, New York), Vol. 125, p. 149–157, 1980.
20. Irwin, L. N., Michael, D. B. and Irwin, C. C. (1980) Ganglioside patterns of fetal rat and mouse brain. *J. Neurochem.* 34:1527.
21. Portoukalin, J., Zwingelstein, G. and Dore, J. (1979) Lipid composition of human malignant melanoma tumors at various levels of malignant growth. *Eur. J. Biochem.* 95:19.
22. Eisinger, M. and Marko, O. Selective proliferation of normal human melanocytes in vitro in the presence of phorbol ester and cholera toxin. *Proc. Natl. Acad. Sci. USA (in press)*.
23. Wooley, D. W. and Gommi, B. W. (1965) Serotonin reseptors VII. Activities of various pure gangliosides as receptors *Proc. Natl. Acad. Sci. USA* 53:959.
24. Tamir, H., Brunner, W., Casper, D. and Rapport, M. M. (1980) Enhancement by gangliosides a binding of serotonin to serotonin binding proteins. *J. Neurochem.* 34:1719.
25. Reif, A. E. and Allen, J. M. V. (1964) The AKR thymic antigen and its distribution in leukemias and nervous tissue. *J. Exp. Med.* 120:413.
26. Keenan, T. W., Morre, D. J. and Basu, S. (1975) Ganglioside biosynthesis. Concentration of glycophingolipid glycosyl transferases in Golgi apparatus from rat liver. *J. Biol. Chem.* 249:310.
27. Pucuszka, T., Duffard, R. O., Nishimur, R. N., Brady, R. P. and Fishman, P. H. (1979) Biosynthesis of bovine thyroid gangliosides. *J. Biol. Chem.* 253:5839.
28. Hakomori, S. (1973) Glycolipids of tumor cell membrane. *Adv. Cancer Res.* 18:265.
29. Silver, H. K. B., Karim, K. A., Archibald, E. L. and Salinas, F. A. (1979) Serum sialic acid and sialyltransferase as monitors of tumor burden in malignant melanoma patients. *Cancer Res.* 39:5036.
30. Lloyd, K. O., Travassos, L. R., Takahashi, T. and Old, L. J. (1979) Cell surface glycoproteins of human tumor cell lines: unusual characteristics of malignant melanoma. *J. Natl. Cancer Inst.* 63:623.
31. Svennerholm, L. (1963) Chromatographic separation of human brain gangliosides. *J. Neurochem.* 10:613.
32. Yu, R. K. and Ando, S. (1980) Structures of some new gangliosides of fish brain in Structure and Function of Ganglioside (ed. L. Svennerholm). Advances in Experimental Medicine and Biology 125:33 (Plenum Press) New York.

TABLE I

Affect of neuraminidase and β-galactosidase on the reactivity of monoclonal antibodies with SK-MEL-28 melanoma cells

| Antibody[1] | IgG Class[1] | Heat sensitivity of antigens[1] | Untreated[2] | Neuraminidase treated[2] | β-Glactosidase treated[2] |
|---|---|---|---|---|---|
| | | | PERCENT POSITIVE CELLS | | |
| $R_{24}$ | IgG3 | Stable | 100 | <10 | 100 |
| $C_5$ | IgG3 | Stable | 100 | <10 | 100 |
| $N_9$ | IgG1 | Sensitive | 100 | 100 | 100 |
| $I_{12}$ | IgG2b | Sensitive | 100 | 100 | 100 |

[1] From Dippold et al. (1). $AbN_9$ precipitates a glycoprotein antigen with a molecular weight of 150,000 and $AbI_{12}$ precipitates a glycoprotein antigen with a molecular weight of 95,000.
[2] Results of direct tests with $AbR_{24}$ (1:5000) tested on enzyme treated cells with the PA- or Ig-MHA assays.

TABLE II

Reactivity of $AbR_{24}$ with gangliosides isolated from various cell lines and tissues as determined by four serological test systems[1]

| Source of gangliosides | Passive hemaggln.[2] | Inhib.[3] | GMIA[4] | $^{125}$I-PA TLC[5] |
|---|---|---|---|---|
| Melanoma (surgical specimens): | | | | |
| MEL-MU | + | + | + | + |
| MEL-JI | + | + | + | + |
| MEL-LO | + | + | + | |
| Melanoma Cell Lines: | | | | |
| SK-MEL-13 | | + | + | |
| SK-MEL-21 | | + | + | |
| SK-MEL-28 | + | + | + | + |
| SK-MEL-31 | | + | + | |
| SK-MEL-37 | + | + | + | |
| SK-MEL-64 | | | + | |
| SK-MEL-93 | | + | + | |
| MeWo | + | + | + | + |
| Carcinoma Cell Lines: | | | | |
| RENAL | | | | |
| SK-RC-7 | − | − | − | + |
| SK-RC-11 | | | − | |
| BLADDER | | | | |
| 253J | | − | − | |
| T-24 | | − | − | + |
| RT-4 | | − | + | + |
| LUNG | | | | |
| SK-LC-LL | − | | − | + |
| CERVIX | | | | |
| ME-180 | − | | − | + |
| COLON | | | | |
| HT-29 | − | | − | |
| Other Cells and Tissues: | | | | |
| ASTROCYTOMA CELL LINES | | | | |
| AJ | | | + | |
| AS | | − | | |
| MOLT-4 (leukemia cell line) | | + | + | + |
| RAJI (lymphoma cell line) | | − | + | |
| BRAIN | | | | |
| Bovine | − | − | − | + |
| Mouse | − | − | − | + |
| Fish | − | − | | |
| Human (adult) | − | − | − | + |
| Human (fetal 10 wks) | | + | +− | |
| Human (fetal 12 & 22 wks) | − | − | | + |
| CHOROID (bovine) | − | + | + | |
| EYE | | | | |
| Mouse | − | + | + | + |
| Fish | − | − | | + |
| LIVER | | | | |
| Mouse | − | − | | + |
| Human (fetal) | − | − | − | |
| Human (adult) | | − | − | |
| SPLEEN | | | | |
| Mouse | | − | − | |
| Human (fetal) | | − | − | |
| Human (adult) | − | − | − | + |
| MUSCLE (fetal human) | | − | + | + |
| KIDNEY | | | | |
| Mouse | − | − | − | + |
| Human (adult) | − | − | − | + |
| HEART (mouse) | − | − | − | + |
| THYMUS (mouse) | − | − | − | |
| LUNG | | | | |
| Mouse | − | − | − | |
| Human (fetal or adult) | − | + | + | + |
| UMBILICUS ERYTHROCYTES | | + | | |
| Human (A & B) | | + | | |
| Human (O) | − | | | |
| Horse | − | | − | + |
| Sheep | − | | − | |
| Cat | − | | + | |
| PLACENTA (human) | − | − | − | + |
| Gangliosides: | | | | |
| $R_{24}$-reactive glycolipid | + | + | + | + |
| $G_{D3}$ | | | + | + |
| $G_{M1}$ | − | − | − | − |
| $G_{M2}$ | − | − | − | − |
| $G_{M3}$ | − | − | − | − |
| $G_{D1a}$ | − | − | − | − |
| $G_{T1}$ | − | − | − | |

[1] Cells and tissues are human in origin unless indicated.
[2] Passive hemagglutination with glycolipid-coated RBC. $AbR_{24}$ was used at a dilution of 1:100; a minumum of 5 μg of $G_{D3}$ could be detected.
[3] Inhibition of PA-MHA reactivity of $R_{24}$ antibody (1:80,000) with SK-MEL-28 target cells. Results were scored positive (+) when the degree of rosetting was less than 20%. At this dilution, $AbR_{24}$ could be completely inhibited by 2 μg of $G_{D3}$.
[4] Glycolipid-mediated immune adherence (GMIA) assay. A reaction was considered positive when greater than 50% of the surface area of the well was covered by a lawn of protein A-conjugated erythrocytes. $AbR_{24}$ was used at a dilution of 1:1000. With this amount of antibody ~25 ng of $G_{D3}$ could be detected.
[5] $^{125}$I-PA-TLC. In this procedure 6 μg of lipid-bound NANA was separated by TLC and the plate treated with $AbR_{24}$ (1:1500) and $^{125}$I-protein A. Reactive components were detected by autoradiography. This procedure can detect approximately 10-25 ng of $G_{D3}$.

What is claimed:

1. Method for recognition of $G_{D3}$ disialoganglioside in or on a human specimen which comprises contacting a $G_{D3}$ specific monoclonal antibody derived by immunization with SK-MEL-28 (deposited as ATCC HTB72) human melamona immunogen with a human test specimen and assaying for the presence or absence of an immune complex formation between said $G_{D3}$-specific antibody and the human test specimen.

2. Method of claim 1 wherein the human test specimen is selected from the group consisting of melanoma, melanocyte, brain and astrocytoma specimens.

3. Method of claim 1 wherein the presence or absence of the immune complex formation is assayed using an assay selected from the group consisting of $^{125}$I-protein A-thin layer chromatography, glycolipid-mediated immune adherence, inhibition of rosetting and passive hemagglutination assays.

4. Method of claim 1 wherein the human test specimen is a malignant melanoma and the presence or absence of the immune complex formation is assayed for using passive hemagglutination or inhibition of rosetting.

5. Method of claim 1 in which the $G_{D3}$ monoclonal antibody is derived from the human melanoma cell line immunogen SK-MEL-28 by forming hybridoma cells between mouse myeloma cells and spleen cells from animals immunized with SK-MEL-28.

6. Method for the recognition of $G_{D3}$ disialoganglioside in a human test specimen having elevated ganglioside or elevated $G_{D3}$ glypolipid levels which comprises reacting a $G_{D3}$ specific monoclonal antibody derived by immunization with SK-MEL-28 (deposited as ATCC HTB72) human melanoma immunogen with a human test specimen selected from the group consisting of melanoma, melanocyte, brain, and astrocytoma specimens and observing the presence or absence of an immune complex formation.

7. Method for determination of the presence of $G_{D3}$ disialoganglioside in human melanoma or melanocyte cells in a human test specimen which comprises reacting a $G_{D3}$ specific monoclonal antibody derived by immunization with SK-MEL-28 (deposited as ATCC HTB72) human melanoma immunogen with the test specimen and observing the presence or absence of an immune complex formation.

8. Method for the diagnosis of melanoma characterized by the presence of $G_{D3}$ disialoganglioside in a human test specimen which comprises reacting a $G_{D3}$ specific monoclonal antibody derived by immunization with SK-MEL-28 (deposited as ATCC HTB72) human melanoma immunogen with a melanoma test specimen and observing the presence or absence of an immune complex formation.

9. Method for the diagnosis of disorders characterized by elevated ganglioside levels in humans which comprises contacting a human test specimen with a suspected elevated ganglioside level with a $G_{D3}$ specific monoclonal antibody derived by immunization with SK-MEL-28 (deposited as ATCC HTB72) human melanoma immunogen and observing the presence or absence of an immune complex formation.

10. Method of claim 9 wherein the elevated ganglioside level is due to an elevated disialoganglioside level.

11. Method of claim 10 wherein the elevated disialoganglioside level is due to an elevated $G_{D3}$ level.

12. Method of claim 9 wherein the disorder is malignant melanoma.

* * * * *

UNITED STATES PATENT AND TRADEMARK OFFICE
CERTIFICATE OF CORRECTION

PATENT NO. : 4,507,391
DATED : March 26, 1985
INVENTOR(S) : Clifford S. Pukel, et al.

It is certified that error appears in the above-identified patent and that said Letters Patent is hereby corrected as shown below:

Column 1, line 29, "disialogangliodie" should read -- disialoganglioside --.

Col. 2, line 8, after "eye;" insert -- □ --.
Col. 8, line 61, "though" should be -- thought --.
Col. 9, line 2, "malanoma" should be -- melanoma --.
Col. 9, line 19, "Gal[2" should be -- Gal[3 --.

Col. 12, line 41, " " should be -- - --.
in Table II,
last entry,"$G_{T1}$"
rightmost column, Claim 1, line 5, "melamona" should be -- melanoma --.

Signed and Sealed this

Twenty-first Day of January 1986

[SEAL]

Attest:

DONALD J. QUIGG

Attesting Officer   Commissioner of Patents and Trademarks